(12) United States Patent
Cao et al.

(10) Patent No.: US 7,854,947 B2
(45) Date of Patent: Dec. 21, 2010

(54) PERSONAL CARE COMPOSITIONS COMPRISING PLANT FIBER

(75) Inventors: Hongjie Cao, Somerville, NJ (US); Gary T. Martino, Monmouth Junction, NJ (US); Joanne Golas, Raritan, NJ (US)

(73) Assignee: Akzo Nobel N.V., Arnhem (NL)

( * ) Notice: Subject to any disclaimer, the term of this patent is extended or adjusted under 35 U.S.C. 154(b) by 1661 days.

(21) Appl. No.: 11/016,031

(22) Filed: Dec. 17, 2004

(65) Prior Publication Data

US 2006/0134045 A1 Jun. 22, 2006

(51) Int. Cl.
*A61Q 5/02* (2006.01)
*A61Q 19/10* (2006.01)

(52) U.S. Cl. .................... 424/750; 424/70.11

(58) Field of Classification Search ........................ None
See application file for complete search history.

(56) References Cited

U.S. PATENT DOCUMENTS

| | | | |
|---|---|---|---|
| 4,477,480 A | 10/1984 | Seidel et al. | |
| 5,187,272 A | 2/1993 | Katcher et al. | |
| 5,350,593 A | 9/1994 | LaCourse et al. | |
| 5,653,967 A * | 8/1997 | Murphy | ............ 424/70.1 |
| 5,703,026 A * | 12/1997 | Setser et al. | ............ 510/152 |
| 5,871,756 A | 2/1999 | Jeffcoat et al. | |
| 2004/0219124 A1 * | 11/2004 | Gupta | ............ 424/70.13 |

FOREIGN PATENT DOCUMENTS

EP 0 554 818 B1 6/1998

OTHER PUBLICATIONS

International Cosmetic Ingredient Disctionary and Handbook, T.E. Gottschalack and G. N. McEwen, Jr., Ph.D., J.D. editors, 10th Ed., vol. 4, pp. 2063-2174 (2003).
International Cosmetic Ingredient Disctionary and Handbook, T.E. Gottschalack and G. N. McEwen, Jr., Ph.D., J.D. editors, 10th Ed., vol. 4, pp. 2177-2299 (2003).
International Cosmetic Ingredient Disctionary and Handbook, T.E. Gottschalack and G. N. McEwen, Jr., Ph.D., J.D. editors, 10th Ed., vol. 4, pp. 2301-2402 (2003).
"AOAC Official Method 991.43 Total, Soluble, and Insoluble Dietary Fiber in Foods," AOAC International, 32.1.17 (First Action, 1991).
Feedstuffs Analysis, "Starch," Analytical methods of the Member Companies of the Corn Refiners Assoication, Inc., pp. G-28-1 to G-28-3 Accepted Nov. 8, 1954; Revised Apr. 15, 1986.

* cited by examiner

*Primary Examiner*—Jyothsna A Venkat
(74) *Attorney, Agent, or Firm*—James C. Abruzzo

(57) ABSTRACT

Personal care compositions having plant fiber such as tapioca fiber, and methods of applying those formulations. The addition of fiber to personal care formulations can provide performance improvement such as cleansing, exfoliation, irritation reduction, suspending, foam enhancement, and rheological property modification.

10 Claims, No Drawings

PERSONAL CARE COMPOSITIONS COMPRISING PLANT FIBER

BACKGROUND OF THE INVENTION

1. Technical Field

The present invention relates to the use of plant fiber in personal care compositions and to methods of using those compositions. More particularly, the invention relates to the use of tapioca fiber in personal care applications for cleansing, exfoliating, irritation reduction, suspending, thickening, and aesthetics and foam property enhancement.

2. Background Information

The term "tapioca" is commonly used to refer to both the tapioca (or cassava) plant and the granular starch that is extracted from the tapioca plant. The tapioca plant is a member of the Euphorbiaceae or spurge family, *manihot* genus, and is grown in countries with tropical climates (e.g., Central and South America, Africa, the West Indies, India and Thailand). The cassava plant has several synonyms, including cassara manioc, manihot, brazilian arrowroot, cassaya starch, and janipha manihot.

Tapioca fiber is a by-product of tapioca starch production. It is usually tan colored solids or particulates with relatively uniform size and shape. It can be used in a wide variety of personal care applications such as to provide deep cleansing and skin exfoliation while reducing skin irritation. Tapioca fiber can also improve formulation aesthetics on skin, provide thickening and suspending properties in aqueous systems, and enhance foam properties in foaming products.

Use of tapioca fiber has been described in other areas such as in adhesives for corrugating. It is also known that tapioca fiber can be used as a dietary fiber supplement in food, with processes having been developed to provide high total dietary fiber therefrom. Use of tapioca flour in cosmetics has been at least briefly mentioned in the art, particularly for use in dusting and facial powders.

Improvement in the performance of most personal care products might be made in a variety of ways, including increasing efficacy, adding functionality, reducing cost, or removing unwanted negative properties. The means by which a formulator may accomplish these improvements vary, but one such means is through novel functional ingredients. It has now been discovered that plant fiber, including tapioca fiber, is one such novel ingredient useful in improving personal care formulations.

SUMMARY OF THE INVENTION

The present invention relates to personal care formulations containing plant fiber, including tapioca fiber, and methods of applying those formulations. In one aspect, the invention relates to the use of tapioca fiber in personal care applications for cleansing, exfoliating, irritation reduction, suspending, thickening, aesthetics and foam property enhancement.

In personal care formulations containing exfoliating or deep cleansing particulates, thickening and suspending agents are needed to keep the particulates suspended and ensure formulation stability. Tapioca fiber can function as both a thickening and suspending agent. The fiber absorbs water and thickens aqueous systems. It can also suspend itself with appropriate use level and viscosity, as well as suspend other solid particles. These thickening and suspending properties of tapioca fiber provides ease in formulating, as well as cost savings, since less or no other thickening and/or suspending agents are required.

Fiber added to a cleansing formulation can absorb dirt, dead skin cells, makeup or other impurities from the skin during cleansing, allowing these impurities to be subsequently rinsed off. For example, in facial masks/packs fiber can aid in building the structure of the mask/clay pack and then aid in exfoliating and deep cleansing upon removal. In foaming cleansing products, fiber can provide foam enhancement. With fiber added to the cleansing product, foams are easier and quicker to form, with foam volume and foam stability improved.

In addition to its exfoliating and deep cleansing benefits, fiber can turns soft and gentle in water containing formulations, providing aesthetically enhanced sensory/skin feel characteristics. For example, no grittiness or harshness is detected when fiber is used in personal care applications.

Fiber is also inert, and therefore demonstrates good compatibility with other ingredients. It is also thermally stable.

The terms below have the following meanings as used herein—

"Surfactant" refers to an ingredient used in a cosmetic formulation that exhibits the ability to reduce the interfacial tension between two immiscible substances, wet skin and hair surfaces, emulsify or solubilize oils, and/or suspend soil. It can include amphoteric, anionic, cationic, and nonionic surfactants.

"Solvent" refers to those liquids that will at least partially dissolve another liquid or a solid at 25° C.

"Aqueous solvent" refers to a solvent containing at least 2 percent water based on total weight of solvent.

"Non-aqueous solvent" refers to a solvent containing less than 2 percent water based on total weight of solvent.

"Cosmetic" refers to those products intended for use on skin, nail and/or hair.

"Cosmetic ingredient" refers to those ingredients that can be used in cosmetics and/or personal care formulations.

"Pigment" refers to those ingredients that can change the color of a formulation.

"Dietary fiber" means total plant fiber, insoluble and soluble, excluding other materials such as protein, starch, and moisture that may be present.

"Fiber" refers to dietary fiber plus any other materials, if any, which may be present in the raw material as produced such as starch, protein and moisture.

"Fragrance" refers to those cosmetic ingredients added to a formulation for the purpose of adding or covering an odor.

"Mousse" refers to a personal care product in which the ingredients foam when dispensed from their container without any mechanical action from the user except possibly the shaking of the product in the container prior to actuation of a valve and subsequent dispensing of the internal contents by actuation.

"Shampoo" refers to a cleansing product containing surfactants that is massaged into wet hair, usually thereby creating foam, which is then rinsed from the hair with water, removing at least some soil and/or oils from the hair.

"Bodywash" refers to a cleaning product distributed over skin, usually thereby creating foam, which is then rinsed from the skin with water removing at least some soil and/or oils from the body.

"Bar soap" refers to a cleaning product in the form of a solid or semi-solid bar containing surfactants and intended for cleaning skin and/or hair.

"Lotion" refers to a composition below about 20,000 centipoise at 25° Celsius ("C") and standard pressure that is applied to skin to provide a cosmetic benefit.

"Cream" refers to a composition having a viscosity equal to or greater than about 20,000 centipoise at 25° C. and standard pressure, and that is applied to the skin to provide a cosmetic benefit.

The term "cosmetic benefit" refers to, but in no way is limited to, such benefits as moisturizing, sun protection, fragrance, wrinkle reduction, and tanning.

"Tapioca" refers to the tapioca or cassava plant.

Accordingly, the present invention provides for a personal care composition that is a cosmetic and includes at least fiber and at least one other cosmetic ingredient therein. These cosmetic ingredients can include, for example, aqueous solvents, non-aqueous solvents, pigments, surfactants, polymers, fragrances or combinations thereof. In one aspect the personal care composition has at least 0.1 percent fiber. In another and further aspect, this fiber can have at least 10% by weight dietary fiber. In even another aspect, the fiber is at least tapioca fiber. Combinations of different fibers are also contemplated. Further, in another embodiment the fiber can be at least a blend of fiber and starch.

In one embodiment, the personal care composition is a cleansing composition. This cleansing composition provides an increase in foaming and/or cleansing versus cleansing compositions without fiber. This cleansing composition can further be an exfoliating cleansing composition. In another aspect, the personal care composition can be, for example, lotions, creams, mousse, body washes, bar soaps, or shampoos.

The present invention is also directed towards a method of cleaning skin or hair that involves applying to the skin or hair a personal care composition having at least fiber and at least one other cosmetic ingredient therein and rinsing the personal care composition from the skin or hair. The fiber can be at least tapioca fiber in one embodiment. In another embodiment the fiber can be at least a blend of fiber and starch.

DETAILED DESCRIPTION OF THE INVENTION

The present invention relates to personal care formulations containing plant fiber, including tapioca fiber, and methods of applying those formulations. The addition of this fiber to personal care formulations can provide performance improvements such as cleansing, exfoliation, irritation reduction, suspending, foam enhancement, and rheological property modification.

Any fiber extracted from plants is suitable for use in this invention. In one embodiment, the fiber is selected from the group consisting of potato, arrowroot, water chestnut, sugar beets, jicama, buckwheat, legumes, millet, milo, barley, oats, corn, teff, rice, cotton seed, bread fruit, pumpkin, winter squash, white squash, plantain, banana, jack fruit and combinations thereof. In another embodiment, the fiber is at least tapioca fiber, and can also include blends of tapioca fiber and other fibers.

Fiber suitable for this invention is often a by-product of starch manufacturing. For example, tapioca starch is obtained from the tuberous root of the tapioca plant and tapioca fiber is obtained from tapioca pulp, which is the by-product of the starch manufacturing process. U.S. Pat. No. 5,350,593 discloses a suitable process for producing tapioca fiber useful in this invention. However, tapioca fiber produced by other processes is also suitable in the invention.

In the present invention and as defined above, fiber products can also contain other ingredients from their production, e.g., starch. In one embodiment, the fiber product contains from about 0 to about 75 percent starch based on the total weight of the product; in another embodiment, the fiber composite contains from about 35 to about 70 percent starch based on the total weight of the product; in another embodiment contains from about 40 to about 60 percent starch; in another embodiment from about 45 to about 53 percent starch.

Fiber according to the invention includes dietary fiber. In one embodiment the total dietary fiber is at least 6 percent based upon the weight of the fiber as produced; in another embodiment the total dietary fiber is at least 10 percent; in another embodiment the total dietary fiber is at least 20 percent; in another embodiment it is at least 30 percent; and in another embodiment it is from about 35 to about 45 percent.

Dietary fiber can include both soluble and insoluble fiber. In one embodiment the weight ratio of soluble to insoluble dietary fiber in the total dietary fiber is from about 1:2 to about 2:1; in another embodiment the ratio is from about 3:2 to about 2:3; in another embodiment from about 4:5 to about 5:4.

The fiber product can also include moisture. Moisture content is determined by comparing the weight difference of the starting fiber versus the fiber after drying in an oven at an elevated temperature until a constant weight is achieved. The oven should be hot enough to drive off the moisture but not so hot as to degrade the tapioca fiber. In one embodiment the water content of the fiber is less than about 25 percent per total weight of the fiber; in another embodiment it is less than about 20 percent; in another embodiment it is less than about 15 percent; in another embodiment the moisture content is less than about 10 percent; in another embodiment the moisture content is from about 10 to about 20 percent; in another embodiment it is from about 12 to about 16 percent.

It is well known that fiber particles can vary in size. In one embodiment at least 90 percent of fiber particles according to the present invention pass through a number 20 mesh screen (850 μm); in another embodiment at least 90 percent pass through a number 40 mesh screen (425 μm); in another embodiment at least 90 percent pass through a number 60 mesh screen (250 μm); in another embodiment at least 90 percent pass through a 100 mesh screen (150 μm).

Fiber according to the present invention can also be treated for reduction of microbiological content by any standard means known in the art such as, but not limited to, irradiation, treatment with active oxygen such as peroxides and peracids, ethylene oxide treatment and ozone gas treatment.

The fiber can be modified using any number of modification techniques known in the art, including physical, chemical and/or enzymatic modifications, in order to obtain the desired attributes. Examples of physical modifications include grinding, extrusion, shearing and thermal-inhibition. Chemical modifications include, for example, crosslinking; acetylation or organic esterification; hydroxyethylation and hydroxypropylation; phosphorylation and inorganical esterification; modifications to make cationic, anionic, nonionic, amphoteric or zwitterionic; modification to make succinates and their derivatives; and conversion by oxidation, enzyme action, acid hydrolysis, and heat.

Any fiber or fiber blend having suitable properties for use herein can be purified by any method known in the art for removing starch off colors native to the fiber or created during processing. An example of a possible treatment is bleaching with active oxygen compounds such as hydrogen peroxide, hypochlorite, and peracids. Other suitable purification processes can be found in the family of patents represented by European Patent No. 0 554 818 B1. Alkali washing techniques are also useful, examples of which are described in the family of patents represented by U.S. Pat. Nos. 4,477,480 and 5,187,272.

Fiber, when used in personal care applications, can offer the benefits of improved deep cleansing and skin exfoliation with reduced irritation, improved formulation skin aesthetics, and improved thickening and suspending properties in aqueous systems. Additional benefits include, for example, foam enhancement in foaming products such as an increase in speed at which the foam forms, as well as an improvement in the volume and stability of the foam once formed. In application, unlike other exfoliating ingredients, fiber turns soft in water, and therefore may feel less gritty or harsh when used.

In personal care applications the percentage of fiber can vary in the formulation. In one embodiment, the personal care formulation contains from about 0.01 percent to about 30 percent fiber per total weight of the formulation; in another embodiment from about 0.5 percent to about 20 percent fiber; in another embodiment from about 1 percent to about 15 percent fiber; in another embodiment from about 2 percent to about 10 percent fiber; in another embodiment from about 3 percent to about 10 percent fiber; and in another embodiment from about 3 percent to about 8 percent fiber.

Fiber's properties make it well suited for many personal care applications such as makeup removers, daily facial wash, facial masks or packs, scrub cleansers, foaming cleansers, moisturizing cleansers, shower gels, body washes, bar soaps, dissolvable soap sheets, anti-acne products, and anti-aging products. Additional personal care applications for which fiber may be suited for use include aftershave lotions, baby lotions/oils/powders/creams, baby shampoo, basecoats and undercoats, bath capsules, bath oils/tablets/salts, bath soaps and detergents, beard softeners, blushers, body and hand preparations, bubble baths, cleansing products, colognes and toilet waters, cuticle softeners, deodorants depilatories, eye lotions, eye makeup preparations, eye makeup removers, eye shadows, eyebrow pencils, eyeliners, face and neck preparations, face powders, foot powders and sprays, foundations, fragrance preparations, hair bleaches, hair color sprays, hair coloring preparations, hair conditioners, hair dyes and colors, hair lighteners with color, hair preparations, hair rinses, hair shampoos, hair sprays, hair straighteners, hair tints, hair wave sets, indoor tanning preparations, leg and body paints, lipsticks, makeup bases, makeup fixatives, makeup preparations, manicuring preparations, mascara, men's talcum, moisturizing preparations, nail creams and lotions, nail extenders, nail polish and enamel removers, nail polish and enamels, night skin care preparations, paste masks, perfumes, permanent waves, personal cleanliness products, powders, preshave lotions, rouges, sachets, shampoos, shaving cream, shaving preparations, shaving soap, skin care preparations, skin fresheners, suntan gels/creams/lotions, suntan preparations, tonics, dressings and other hair grooming aids, among others. Specific examples of ingredients typically used in these applications can be found in the *International Cosmetic Ingredient Dictionary and Handbook*, 10$^{th}$ Ed., Vol. 4, pp. 2301-2402, T. E. Gottschalck and G. N. McEwen, Jr., Ph.D., J. D., The Cosmetic, Toiletry, and Fragrance Association, Washington, D.C. (2003).

Fiber is compatible with most ingredients used in personal care applications. These ingredients can include, for example, alcohols, aldehydes, alkanolamides, alkanolamines, alkoxylated alcohols, alkoxylated amides, alkoxlated amines, alkoxylated carboxylic acids, alkyl aryl sulfonates, alkyl ether sulfates, alkyl-substituted amino acids, alkyl sulfates, alkyamido alkylamines, amides, amine oxides, amines, amino acids, benzophenones, betaines, biological polymers and their derivatives, biological products, carbohydrates, carboxylic acids, color additives, elements, essential oils, esters, ethers, fats and oils, fatty acids, fatty alcohols, glyceryl esters and derivatives, gums (hydrophilic colloids and derivatives), halogen compounds, hydrocarbons, imidazoline compounds, inorganic acids, inorganic bases inorganic salts, inorganics, isethionates, ketones, lanolin and lanolin derivatives, organic salts, PABA derivatives, phenols, phosphorus compounds, polymeric ethers, polymers, polyols, protein derivatives, proteins, quaternary ammonium compounds, sarcosinates and sarcosine derivatives, siloxanes and silanes, soaps, sorbitan derivatives, starches, sterols, sulfonic acids, sulfosuccinates and sulfosuccinamates, sulfuric acid esters, synthetic polymers, thio compounds, unsaponifiables, and waxes. Specific examples of ingredients that fall within these chemical classes can be found in the *International Cosmetic Ingredient Dictionary and Handbook*, 10$^{th}$ Ed., Vol. 4, pp. 2063-2174; T. E. Gottschalck and G. N. McEwen, Jr., Ph.D., J. D.; The Cosmetic, Toiletry, and Fragrance Association: Washington, D.C. (2003).

Specific synthetic ingredients with which the fiber of the invention can be used include, for example, AMPHOMER and AMPHOMER LV-71 polymers (octylacrylamide/acrylates/butylaminoethyl methacrylate copolymers), AMPHOMER HC polymer (acrylates/octylacrylamide copolymers) BALANCE 0/55 and BALANCE CR polymers (acrylates copolymer), BALANCE 47 polymer (octylacrylamide/butylaminoethyl methacrylate copolymer), DERMACRYL 79 and DERMACRYL LT polymers (acrylates/ocrylacrylamide copolymer), RESYN 28-2930 polymer (VA/crotonates/vinyl neodecanoate copolymer), RESYN 28-1310 polymer (VA/Crotonates copolymer), FLEXAN polymers (sodium polystyrene sulfonate), DynamX polymer (polyurethane-14 (and) AMP-Acrylates copolymer), RESYN XP polymer (acrylates/octylacrylamide copolymer), STRUCTURE 2001 (acrylates/steareth-20 itaconate copolymer) and STRUCTURE 3001 (acrylates/ceteth-20 itaconate copolymers) (all of the above copolymers commercially available from National Starch and Chemical Company, Bridgewater, N.J.); OMNIREZ-2000 (PVM/MA half ethyl ester copolymer), GANEX P-904 (butylated PVP), GANEX V-216 (PVP/hexadecene copolymer) GANEX V-220 (PVP/eicosene copolymer), GANEX WP-660 (tricontanyl PVP), GANTREZ A-425 (butyl ester of PVM/MA copolymer), GANTREZ AN-19 PVM/MA copolymer, GANTREZ ES 225 (ethyl ester of PVM/MA copolymer), GANTREZ ES-425 (butyl ester of PVM/MA copolymer), GAFFIX VC-713 (vinyl caprolactam/PVP/dimethylaminoethyl methacrylate copolymer), GAFQUAT 755 (polyquaternium-11), GAFQUAT HS-100 (polyquaternium-28) AQUAFLEX XL-30 (Polyimide-1), AQUAFLEX SF-40 (PVP/Vinylcaprolactam/DMAPA Acrylates Copolymer), AQUAFLEX FX-64 (Isobutylene/Ethylmaleimide/Hydroxyethylmaleimide Copolymer), ALLIANZ LT-120 (Acrylates/C1-2 Succinates/Hydroxyacrylates Copolymer), STYLEZE CC-10 (PVP/DMAPA Acrylates Copolymer), STYLEZE 2000 (VP/Acrylates/Lauryl Methacrylate Copolymer), STYLEZE W-20 (Polyquaternium-55), Copolymer Series (PVP/Dimethylaminoethylmethacrylate Copolymer), ADVANTAGE S and ADVANTAGE LCA (Vinylcaprolactam/VP/Dimethylaminoethyl Methacrylate Copolymer), ADVANTAGE PLUS (VA/Butyl Maleate/Isobornyl Acrylate Copolymer) (all of the above copolymers commercially available from ISP, Wayne, N.J.); ULTRAHOLD STRONG (acrylic acid/ethyl acrylate/ t-butyl acrylamide), LUVIMER 100P (t-butyl acrylate/ethyl acrylate/methacrylic acid), LUVIMER 36D (ethyl acrylate/t-butyl acrylate/methacrylic acid), LUVIQUAT HM-552 (polyquatemium-16), LUVIQUAT HOLD (polyquaternium-16), LUVISKOL K30 (PVP) LUVISKOL K90 (PVP), LUVISKOL VA 64 (PVP/VA copolymer) LUVISKOL VA73W (PVP/VA copolymer), LUVISKOL VA, LUVISET PUR (Polyurethane-1), LUVISET Clear (VP/Methacrylamide/Vinyl Imidazole Copolymer), LUVIFLEX SOFT (Acrylates Copolymer), ULTRAHOLD 8 (Acrylates/Acrylamide Copolymer), LUVISKOL Plus (Polyvinylcaprolactam), LUVIFLEX Silk (PEG/PPG-25/25 Dimethicone/Acrylates Copolymer) (all of the above copolymers commercially available from BASF, ); AMERHOLD DR-25 (acrylic acid/methacrylic acid/acrylates/methacrylates, commercially available from Amerchol Corporation, a subsidiary of The Dow Chemical Company, Midland, Mich.); ACUDYNE 258 (acrylic acid/methacrylic acid/acrylates/methacrylates/hydroxy ester acrylates copolymer, commercially available from Rohm and Haas, Philadelphia, Pa.); DIAFORMER Z-301, DIAFORMER Z-SM, and DIAFORMER Z-400 (methacryloyl ethyl betaine/acrylates copolymer), ACUDYNE 180 (Acrylates/Hydroxyesters Acrylates Copolymer), ACUDYNE SCP (Ethylenecarboxyamide/AMPSA/Methacrylates Copolymer), and the ACCULYN rheological modifiers (all of the above commercially available from Clariant, Muttenz, Switzerland); FIXOMER A-30 and FIXOMER N-28 (INCI names: methacrylic acid/sodium acrylamidomethyl propane sulfonate copolymer, commercially available from ONDEO Nalco, Naperville, Ill.); FIXATE G-100 (AMP-Acrylates/Allyl Methacrylate Copolymer), FIXATE PLUS (Polyacrylates-X), CARBOPOL Ultrez 10 (Carbomer), CARBOPOL Ultrez 20 (Acrylates/C10-30 Alkyl Acrylates Copolymer), AVALURE AC series (Acrylates Copolymer), AVALURE UR series (Polyurethane-2, Polyurethane-4, PPG-17/IPDI/DMPA Copolymer) (all of the above commercially available from Noveon, a wholly owned subsidiary of The Lubrizol Corporation, Cleveland, Ohio); polyethylene glycol; water-soluble acrylics; water-soluble polyesters; polyacrylamides; polyamines; polyquaternary amines; styrene maleic anhydride (SMA) resin; polyethylene amine; and other conventional polymers.

Examples of commercial starches, with their INCI names, with which the fiber of the present invention can be used include, for example, the AMAZE® polymer (corn starch modified), CELQUAT® LS-50 resin (polyquatemium-4/hydroxypropyl starch copolymer), STRUCTURE® XL polymer (hydroxypropyl starch phosphate), DRY FLO®PC lubricant (aluminum starch octenyl succinate), DRY FLO® AF lubricant (corn starch modified), DRY FLO® ELITE LL lubricant (aluminum starch octenyl succinate (and) lauryl lysine), DRY FLO® ELITE BN lubricant (INCI name: aluminum starch octenyl succinate (and) boron nitride), PURITY®21C starch (zea maize (corn) starch), TAPIOCA PURE (tapioca starch), NATRASORB W and NATRASORB BATH (tapioca starch), NATRASORB HFB (aluminum starch octenyl succinate (and) acrylates polymer (and) magnesium carbonate), INDEX (dextrin), thermally inhibited corn, potato, tapioca, high amylase, and waxy maize starches sold under the NOVATION trademark, and resistant starches sold under the HI-MAIZE trademark (all of the above starches commercially available from National Starch and Chemical Company, Bridgewater, N.J.); CROSTYLE MFP (trimethyl quaternized maize starch commercially available from Croda International PLC, East Yorkshire, United Kingdom); SENSOMER C1-50 (starch hydroxypropyltrimonium chloride, commercially available from ONDEO Nalco, Naperville, Ill.).

Other natural polymers with which the fiber of the present invention can be used include, without limitation, cellulosic materials such as carboxymethyl cellulose, hydroxypropyl cellulose, microcrystalline cellulose, ethyl cellulose, cellulose acetate phthalate, cationic cellulose derivatives such as polyquatemium-4 (CELQUAT L-200 and CELQUAT H-100 polymers from National Starch and Chemical Company) and polyquaternium-10 (CELQUAT SC-240C and CELQUAT 230M polymers from National Starch and Chemical Company); gums such as xanthan gum (AMAZETMXT polymer from National Starch and Chemical Company, Bridgewater, N.J.); pullulan; hydrocolloids; carrageenan; alginate; casein; gelatin; and solubilized proteins.

Optional ingredients in personal care applications using fiber can include abrasives, absorbents, adhesives, anti-acne agents, anti-caking agents, anti-caries agents, antidandruff agents, antifoaming agents, antifungal agents, antimicrobial agents, antioxidants, antiperspirant agents, antistatic agents, artificial nail builders, beads, binders, buffering agents, bulking agents, chelating agents, colorants, corn/callus/wart removers, corrosion inhibitors, cosmetic astringents, cosmetic biocides, denaturants, deodorant agents, depilating agents, drug astringents (skin protectant drugs), emulsion stabilizers, epilating agents, exfoliants, external analgesics, film formers, flavoring agents, fragrance ingredients, hair colorants, hair conditioning agents, hair fixatives, hair-waving/straightening agents, humectants, lytic agents, nail conditioning agents, opacifying agents, oral care agents, oral health care drugs, oxidizing agents, pesticides, pH adjusters, plasticizers, preservatives, propellants, reducing agents, skin bleaching agents, skin-conditioning agents (emollients, humectants, occlusives), skin protectants, slip modifiers, solvents, sunscreen agents, surface modifiers, surfactants (cleansing agents, emulsifying agents, foam boosters, hydrotropes, solubilizing agents, suspending agents), suspending agents (nonsurfactant), ultraviolet light absorbers, viscosity controlling agents, viscosity decreasing agents, viscosity increasing agents (both aqueous and nonaqueous), waterproofing agents, heat generating agents and/or effervescing agents, glitter and decorative beads and shapes. Specific examples of ingredients typically used for these functions can be found in the *International Cosmetic Ingredient Dictionary and Handbook* (INCI), $10^{th}$ Ed., Vol. 4, pp. 2177-2299; T. E. Gottschalck and G. N. McEwen, Jr., Ph.D., J. D.; The Cosmetic, Toiletry, and Fragrance Association, Washington, D.C. (2003). Product forms in which the fiber can also be employed include gels, lotions, creams, emulsions, liquids, pastes, solids, sticks, bars, sprays, films or sheets, among others.

When used in the manufacture of personal care formulations such as cosmetics, the fiber can be incorporated into the formulations in a number of ways, some of which can change the properties and performance of the fiber in the formulation. Fiber can be added with or without heat to aqueous or non-aqueous formulations. It can be added to either the oil or water phases of oil-in-water or water-in-oil emulsions, and it can be added to emulsions prior to heating, with heating, during cool down, or after the emulsion has cooled. Fiber can be slurried with other ingredients and then added to a formulation. It can be formed into semi-stable slurries or suspended in solvents. Fiber can be added to a formulation at the end of a formulation process or at any convenient stage therein. Any typical method use to incorporate exfoliants into cosmetic formulations can be applicable.

When used in personal care formulations, any starch present from the fiber can be in either cooked or uncooked form. Whichever form is used can give different properties to the application. For instance, cooked starch can provide, among other properties, thickening and suspending or improve tactile properties such as softness or stickiness. In the uncooked form, the starch can provide the benefits of reduce oiliness or shine, among others.

Fiber containing formulations can be applied to the skin or hair in the manner typically used for those applications.

EXAMPLES

The following examples are presented to further illustrate and explain the present invention and should not be taken as limiting in any regard.

The chemicals contained in the examples are listed using their INCI names or tradenames. The INCI name of an ingredient comes from the *International Cosmetic Ingredient Dictionary and Handbook*, 10th Ed.; T. E. Gottschalck and G. N. McEwen, Jr., Ph.D., J. D.; The Cosmetic, Toiletry, and Fragrance Association, Washington, D.C. (2003). For reference, the tradenames used in the following examples are listed next to their INCI name in the following Table 1.

All percents used are on a weight/weight basis. Standard batching procedures were used to make the formulations in the examples, and the formulations should be repeatable without undue experimentation by someone of normal skill in the art.

In the Examples the chemical ingredients are named according to their INCI names, their tradenames, or both.

Example 1

Test Methods

The following test methods were used in the following examples.

"a" value: The "a" value for a test sample of cleanser is measured by first staining two 6.4×6.4 cm sections of vitro-skin N-19 with a controlled amount of L'Oréal Colour Riche® in Drumbeat Red 310 lipstick. Staining is then followed by application of a controlled amount of the test cleanser sample to the vitro-skin sections and rinsing. The cleansing power of each test sample is then determined by measuring the "a" value for each treated vitro-skin, taking ten measurements of each vitro-skin using a Brightimeter® Model S-5 colorimeter (available from Technidyne Corpora-

TABLE 1

Tradenames of components used in the Examples with their corresponding INCI and/or technical name

| Tradename | INCI Name |
| --- | --- |
| AMAZE ® XT | Dehydroxanthan gum |
| GLYDANT ® Plus ® | DMDM hydantoin and Iodopropynyl Butylcarbamate |
| STEPAN-MILD BSB (42%) | Water, PEG-80 Sorbitanlaurate, cocamidopropyl betaine, disodium trideceth sulfate, disodium lauroamphoacetate, PEG-150 distearate, sodium laureth-13 carboxylate, quaternium-15, tetrasodium EDTA, DMDM hydantoin, citric acid |
| CARBOPOL ® ETD 2020 | Acrylates/C12–30 Alkyl Acrylate Crosspolymer |
| STANDAPOL ® WAQ-LC | Sodium lauryl sulfate |
| INCRONAM 30 | Cocamidopropyl betaine |
| CRODACOL C-70 | Cetyl alcohol |
| COSMOWAX J | Cetearyl alcohol and Ceteareth-20 |
| ARLACEL ® 165 | Glyceryl stearate and PEG-100 |
| CROPURE ® BABASSU | Babassu oil |
| PHENONIP ® | Phenoxyethanol (and) methylparaben (and) ethylparablen (and) butylparaben (and) propylparapen |
| INCROMECTANT LAMEA | Acetamide MEA and Lactamide MEA |
| CROVOL PK-70 | PEG-45 Palm Kernel Glycerides |
| INCROMIDE CAC | Cocamide DEA Cocoyl Sarcosine |
| AJIDEW ® N-50 | Sodium PCA |
| STRUCTURE ® Plus polymer | Acrylates/Amonoacrylates/$C_{10-30}$ Alkyl PEG-20 Itaconate Copolymer |
| PLANATERIN 2000 | Alkyl Polyglucaside |
| UVINUL ® MS-40 | Benzophenone-4 |
| GERMABEN ® II | Propylene Glycol, Diazolidinyl Urea, Methylparaben, Propylparaben |
| DISSOLVINE NA-2X | Disodium EDTA |
| STANDAPOL ® EA-2 | Ammonium Laureth Sulfate |
| STANDAPOL ® A | Ammonium Lauryl Sulfate |
| MONATERIC CAB-LC | Cocamidopropyl Betaine |
| MONASIL ® PLN | Linoleamidopropyl PG-Dimonium Chloride |
| PROMIDIUM ® 2 | PPG-2 Hydroxyethyl Coco/Isosteramide |
| FLORABEADS ® Jojoba | Jojoba Esters |
| ORMAGEL ® SH | Hypnea Musciformis, Gellidiela Acerosa, Sargassum Filipendula, Sorbitol, Propylparaben, Methylparaben |
| CRODALAN AWS | Polysorbate 80, Oleyl Acetate, Cetyl Acetate, Acetylated Lanolin Alcohol, Stearyl Acetate |
| N-LITE ® LP | Food Starch-Modified |
| STRUCTURE ® XL | Hydroxypropyl starch phosphate |
| KATHON ® CG II Biocide | Methylchloroisothiazolinone and Methylisothiazolinone |
| AMISOFT ® CT-12 | TEA-cocoyl glutamate | tion). The higher the "a" value the more red the sample appears. The "a" value is inversely proportional to amount of lipstick removed from the vitro-skin. Therefore, the higher the "a" value, the lower the cleansing power of the sample.

Subjective Performance Evaluations: Subjective performance of the test cleansing formulations was determined by the following procedure. First, L'Oréal Colour Riche® in Drumbeat Red 310 lipstick is applied to a panelist hand. Next, a controlled amount of test cleansing formulation is applied. The hand is then washed and rinsed, controlling the amount of scrubbing per sample. Each evaluation is conducted by eight panelists. Statistical analysis is run at the 95% confidence level to determine differences between samples.

Starch Deposition Testing: Starch deposition was determined by measuring the deposition on wool swatches, because the chemical and structural properties of wool mirror those of human hair and skin. Therefore, deposition on wool correlates to deposition on human hair and skin. Testing was conducted by treating a specific size wool swatch with a controlled amount of a test composition and then rinsing the swatch in controlled manner. After rinsing, the swatch is observed for residual product. If there is no visible residual product, the swatch is then treated with an iodine indicator that will color any starch. Deposition is determined visually by observing color change.

Foam Testing: The impact of tapioca fiber on foam quality was measured using the following procedure. First the flash foam (the amount of foam appearing from a cleanser during use with initial agitation and shear) is measured by adding to a warm (approximately 40.6° C.) 500 ml graduated cylinder a 40.6° C. mixture of 15.0 grams of test formulation and 85.0 grams of hard water, which consists of deionized water containing 0.0204 percent of magnesium pentahydrate and 0.0220 percent of calcium chloride dihydrate. Next, the cylinder is sealed to prevent leakage and inverted and then turned back upright to complete 1 cycle by an agitator. This is repeated for 20 cycles, with the agitator stopped to measure the foam height after 4 and 20 cycles. After the twentieth cycle, the agitator is stopped and a stopwatch started to measure drain time, which is a measure of foam stability. Drain time is the time in seconds that it takes the water level in the cylinder to reach 100 ml after it has been turned upright again.

Total, Soluble, and Insoluble Dietary Fiber: The amount of total, soluble, and insoluble dietary fiber present in the tapioca fiber samples were determined using AOAC Method 991.43, Association of Analytical Communities, "Total, Soluble, and Insoluble Dietary Fiber in Foods" (First Action, 1991).

Starch content: The percentage of starch present in tapioca fiber samples is measured using a polarimeter (Model 141, obtained from Perkin-Elmer, Norwalk, Conn.). This procedure is a modification of the "Feedstuffs Analysis Procedure for Starch" (G-28) of the Standard Analytical Methods of the Member Companies of the Corn Refiners Association, Inc., 2nd Revision, Apr. 15, 1986. In this modified procedure, a 2% by weight solution of tapioca fiber in 40 percent dihydrate calcium chloride solution is cooked in a beaker in a boiling water bath for 30 minutes. The beaker contents are restored to their original weight by the addition of the calcium chloride solution and the sample are filtered on a Buchner funnel fitted with glass fiber filter paper. The filtrate is collected and the optical rotation of the filtrate is measured with a polarimeter.

Cold Water Solubility: The solubility of a sample in cold water is determined by making a 5% dispersion in cold water and making visual observations for precipitate and solubility.

Hot Water Solubility: Hot water solubility is determined by making a 5% dispersion of the sample to be tested in water. The water-sample mixture is then heated to between 80-90° C. with mixing and held at that temperature for 30 minutes. At the end of the 30 minutes of heating and mixing, the samples are visually observed for differences in suspendability, solubility, rheology, pH and viscosity. Viscosity is measured using a Brookfield DV-1 viscometer with a number 6 spindle at 20 rpm.

Solubility by Settling: Solubility by settling is determined by dispersing 5.1 grams of sample in 96.9 grams of deionized water. The water-sample mix is then heated in an 80-90° C. water bath for 30 minutes, with mixing the first 10 minutes. The sample is removed from the hot water bath and 100 ml is immediately poured into a 100 ml graduated cylinder. The cylinder is covered and left to stand overnight at room temperature. The next day the insoluble fraction is measured in ml in the graduated cylinder.

Example 2

Effect on Foaming Properties in Fiber-Containing Formulations

Table 2 demonstrates the beneficial effects on foaming of tapioca fiber in a cleansing formulation.

TABLE 2

Comparison of foam properties of a cleansing formulation with and without tapioca fiber in the formulation

| Ingredients Tradename/ INCI Name | INCI Name | Weight Percent A | Weight Percent B |
|---|---|---|---|
| Deionized Water | Water | 70.95 | 70.95 |
| Disodium EDTA | Disodium EDTA | 0.05 | 0.05 |
| AMAZE ® XT gum | Dehydroxanthan gum | 1.50 | 1.50 |
| GLYDANT ® Plus | DMDM hydantoin and Iodopropynyl Butylcarbamate | 0.50 | 0.50 |
| STEPAN-MILD BSB (42%) | Water, PEG-80 Sorbitanlaurate, cocamidopropyl betaine, disodium trideceth sulfate, disodium lauroamphoacetate, PEG-150 distearate, sodium laureth-13 carboxylate, quaternium-15, tetrasodium EDTA, DMDM hydantoin, citric acid | 20.00 | 20.00 |
| Tapioca fiber | | 7.00 | 0.00 |
| | Flash Foam (ml) 4 cycles | 257 | 240 |
| | Flash Foam (ml) 20 cycles | 340 | 332 |
| | Drain Time (sec) | 14 | 13 |

Formulation A and B demonstrate the difference in foam properties achievable by adding tapioca fiber to a formulation. Formulation A, which includes fiber, provided an increase in flash foam versus Formulation B without the added fiber.

Example 3

Subjective Evaluations of Formulation Containing Tapioca Fiber

Table 3 and Table 4 below demonstrate the subjective benefits to using tapioca fiber in a personal care cleansing formulation.

TABLE 3

Comparison of Formula A to Formula B of Example 2 for subjective efficacy and properties

| Property | Sample Chosen | |
|---|---|---|
| | Example 2, Formula A (with tapioca fiber) | Example 2, Formula B (no tapioca fiber) |
| Cleansing efficacy | X | |
| Foaming | X | |

"X" indicates the sample chose as superior.

TABLE 4

Comparison of Formula A of Example 2 to Commercial Product (St. Ives Apricot Scrub with walnut shell powder for exfoliation)

| Property | Sample Chosen | |
|---|---|---|
| | Example 2, Formula A (with tapioca fiber) | St. Ives Apricot Scrub |
| Cleansing efficacy | X | |
| Less irritation/harshness | X | |
| After feel (smooth and soft) | X | |
| Overall Preference | X | |

"X" indicates the sample chose as superior.

Example 4

Tapioca Fiber Cleansing Properties

The following 2 formulations in Table 3 were evaluated versus commercial products for cleansing efficacy, and the results of this testing are in Table 4 below.

TABLE 5

Cleansing formulations used to demonstrate improved cleansing efficacy of formulations with fiber versus formulations without fiber

| Ingredients Tradename/INCI Name | Weight Percent C | Weight Percent D |
|---|---|---|
| Part A | | |
| Deionized Water | 78.00 | 77.75 |
| Disodium EDTA | 0.05 | 0.05 |
| CARBOPOL ® ETD 2020 | 0.20 | 0.20 |
| Glycerin | 3.00 | 3.00 |
| STANDAPOL ® WAQ-LC | 2.00 | 2.00 |
| INCRONAM 30 | 1.50 | 1.50 |
| Part B | | |
| Stearic acid | 2.00 | 2.00 |
| Glycol distearate | 1.00 | 1.00 |
| CRODACOL C-70 | 0.75 | 0.75 |
| COSMOWAX J | 0.75 | 0.75 |
| ARLACEL ® 165 | 0.75 | 0.75 |
| CROPURE BABASSU | 0.50 | 0.50 |
| Caprylic/Capric Triglyceride | 1.50 | 1.50 |
| Part C | | |
| Triethanolamine (99%) | to pH 5.5 | to pH 5.5 |
| Part D | | |
| PHENONIP ® | 1.00 | 1.00 |
| Tapioca Fiber | 7.00 | 0.00 |
| Eucalyptus oil | 0.00 | 0.15 |
| Camphor oil | 0.00 | 0.10 |

Formulations C and D demonstrate the formulation of tapioca fiber into a cleansing formulation. The cleaning power of both formulations is compared in Table 6 below.

TABLE 6

Comparison of deep cleansing efficacy of formulations with and without fiber

| Sample | Sample Description | "a" Value |
|---|---|---|
| 1 | Blank | 49.48 |
| 2 | St. Ives Apricot Scrub (no tapioca fiber but with walnut shell powder for exfoliation) | 16.63 |
| 3 | Olay Moisturizing Body Wash with 10% tapioca fiber post-added | 11.34 |
| 4 | Olay Moisturizing Body Wash with no tapioca fiber added | 47.46 |
| 5 | Example 3, Formulation C with 7% tapioca fiber | 24.85 |
| 6 | Example 3, Formulation D with tapioca fiber omitted | 45.79 |

Sample 1 demonstrates the maximum color retention, or the lowest cleansing power.

Sample 2 demonstrates the cleansing power of a commercial product with a commercial material having walnut shells used to exfoliate and deep clean.

Sample 3 demonstrates the increase in cleansing power achieved by adding tapioca fiber to a commercial formulation.

Sample 4 demonstrates the cleansing power of a commercial scrub containing no ingredient to exfoliate.

Sample 5 demonstrates the deep cleansing achieved by formulation with 7 percent of tapioca fiber into a gentle cleanser.

Sample 6 demonstrates the cleansing power of the same formulation as Sample 5 but with no tapioca fiber added.

From the 'a' values determined according to the test method provided in Example 1, it is seen that formulations including fiber greatly improve cleansing efficacy versus formulations without fiber (samples 3 and 5 versus samples 4 and 6, respectively). Further, the results illustrate that fiber provides at least comparable results against other non-fiber exfoliants (walnut powder of sample 1).

Example 5

Comparison of Tapioca Fiber to High Fiber Tapioca Flour

Tapioca flour was prepared according the formula in Table 7 below. The tapioca fiber composition used in making the tapioca flour is listed in Table 8 below.

TABLE 7

Tapioca Flour Formulation

| Ingredients Tradename/INCI Name | Weight (grams) |
|---|---|
| Tapioca Fiber | 15.7 |
| Tapioca Starch | 84.3 |

Tapioca Flour Procedure: 15.7 g of tapioca fiber was mixed together with 84.3 g of native, unmodified tapioca starch in a 1 quart (0.95 liters) jar, and a lid was placed on the jar. The jar was then manually shaken for 3 minutes and placed on moving rollers for 1 hour.

TABLE 8

Tapioca Fiber composition used in Table 7 and in testing below

| Ingredients Tradename/INCI Name | Weight Percent |
|---|---|
| Moisture | 14 |
| Tapioca Starch | 49 |
| Dietary Fiber | 37 |

The tapioca flour of Table 7 was compared to the tapioca fiber of Table 8 for cold and hot water solubility according to the test methods provided in Example 1. The results are tabulated in Table 9 below.

TABLE 9

Cold and Hot Water Solubility Comparison of Tapioca Flour and Tapioca Fiber

| | | Sample Description | |
|---|---|---|---|
| Test Description | | Tapioca Fiber | Tapioca Flour |
| Suspendability | Cold Water | None | None |
| | Hot Water (same day) | None | Uniform/Good |
| | Hot Water (next day) | None | Uniform/Good |
| Solubility | Cold Water | Insoluble | Insoluble |
| | Hot Water (same day) | Mostly Insoluble | Soluble |
| | Hot Water (next day) | Mostly Insoluble | Soluble |
| Rheology | Cold Water | Insoluble | Insoluble |
| | Hot Water (same day) | Insoluble | Gel, with long stringy rheology |
| | Hot Water (next day) | Insoluble | Gel, with long string rheology |
| pH | Cold Water | Insoluble | Insoluble |
| | Hot Water (same day) | 4.7 | 5.0 |
| | Hot Water (next day) | 4.7 | 5.0 |
| Viscosity | Cold Water | Insoluble | Insoluble |
| | Hot Water (same day) | 200 centipoise | 5650 centipoise |
| | Hot Water (next day) | 200 centipoise | 6550 centipoise |

The above Table 9 illustrates the very different properties and performances of tapioca flour and tapioca fiber. For example, from the above table it is seen that where tapioca flour has good suspendability and is soluble in hot water, tapioca fiber is not. Further, whereas tapioca flour forms gel or gel-like rheology after mixing in hot water, tapioca fiber is insoluble and does not. Finally, whereas the tapioca flour builds significant viscosity after mixing in hot water, tapioca fiber does not. Therefore, one would recognize that tapioca flour and tapioca fiber would provide very different properties and performance when used in personal care or cosmetic products. Other differences one would expect to see include difference in Theological properties, on-skin aesthetics, cleansing, and exfoliating.

The tapioca fiber and tapioca flour were compared by comparing the performance in solubility by settling according to the test method provided in Example 1. The results are tabulated in Table 10 below.

TABLE 10

Solubility by settling results for tapioca flour and tapioca fiber

| Sample Description | Insoluble Fraction (ml) |
|---|---|
| Tapioca Fiber | 83 |
| Tapioca Flour | 100 |

The cleansing properties of tapioca fiber were compared to those of tapioca flour by adding the two materials to a commercial cleansing product. The tapioca fiber and tapioca flour compositions described in Table 7 and Table 8 above were formulated into cleansing products and compared for cleansing power as described in Table 11 below.

TABLE 11

Cleansing formulations and results of testing for cleansing power

| Ingredients Tradename/ INCI Name | Formulation E (Wt. Percent) | Formulation F (Wt. Percent) | Formulation G (Wt. Percent) |
|---|---|---|---|
| Olay Complete Body Wash (sensitive skin) | 90.00 | 90.00 | 100.00 |
| Tapioca Fiber | 10.00 | 0.00 | 0.00 |
| Tapioca Flour | 0.00 | 10.00 | 0.00 |
| Total | 100.00 | 100.00 | 100.00 |
| "a" Value | 10.41 | 27.39 | 51.31 |

From the above it is seen that tapioca fiber provides the best cleansing of the three formulations, with tapioca flour also providing an improved cleansing over the commercially available product. Still, basic differences exist between tapioca fiber and tapioca flour that can affect which ingredient is added to a formulation. These differences include solubility, gelling, rheology, suspendability and, as illustrated above, performance in personal care products.

Example 6

Tapioca Fiber in an Exfoliating Cleansing Bar Formulation

TABLE 12

Cleansing Bar Formulation

| Ingredients Tradename/INCI Name | Weight Percent |
|---|---|
| Part A | |
| TEA lauryl sulfate | 17.00 |
| INCROMECTANT LAMEA | 5.00 |
| CROVOL PK-70 | 9.00 |
| INCROMIDE CAC | 19.00 |
| Propylene Glycol | 9.00 |
| Glycerin | 10.00 |
| Part B | |
| Sodium Stearate | 24.00 |
| Part C | |
| Urea | 2.00 |
| Part D | |
| Tapioca Fiber | 5.00 |

Procedure: Mix together Part A ingredients and heat to 85-90° C. Slowly add Part B with mild agitation so as to avoid excessive foaming. Add Part C with mixing while maintaining the temperature between 85° C. and 90° C. When all solids are dissolved, stop heating and add Part D. After evenly dispersing Part D by slow agitation, allow the formulation to stand at 85° C. to allow for deaeration. Foam is then skimmed off, with the remaining mixture poured into suitable molds.

Example 6A

Example 6 is repeated with corn fiber in place of tapioca fiber.

Example 6B

Example 6 is repeated with rice fiber in place of tapioca fiber.

Example 6C

Example 6 is repeated with sago fiber in place of tapioca fiber.

Example 6D

Example 6 is repeated with pea fiber in place of tapioca fiber.

Example 6E

Example 6 is repeated with wheat fiber in place of tapioca fiber.

Example 6F

Example 6 is repeated with oat fiber in place of tapioca fiber.

Example 7

Tapioca Fiber Dissolvable Soap Sheet

TABLE 13

| Soap Sheet Formulation | |
|---|---|
| Ingredients Tradename/INCI name | Weight Percent |
| Deionized Water | 39.80 |
| N-LITE LP | 16.80 |
| Herbal Essences Moisturizing Body Wash | 32.20 |
| Glycerin | 7.00 |
| GERMABEN II | 0.50 |
| Tapioca Fiber | 3.70 |

Procedure: all ingredients are combined in order in water, mixing each until homogeneous. The resulting mixture is then formed into a film and dried to remove enough moisture to make the film into a peelable sheet.

Example 7A

Example 7 is repeated with corn fiber in place of tapioca fiber.

Example 7B

Example 7 is repeated with rice fiber in place of tapioca fiber.

Example 7C

Example 7 is repeated with sago fiber in place of tapioca fiber.

Example 7D

Example 7 is repeated with pea fiber in place of tapioca fiber.

Example 7E

Example 7 is repeated with wheat fiber in place of tapioca fiber.

Example 7F

Example 7 is repeated with oat fiber in place of tapioca fiber.

Example 8

Tapioca Fiber Shower Gel Cleanser

TABLE 14

| Shower Gel Cleanser Formulation | |
|---|---|
| Ingredients Tradename/INCI name | Weight Percent |
| Part A | |
| Deionized Water | 45.15 |
| Polyquaternium-10 | 0.20 |
| Citric acid | 0.10 |
| Tetrasodium EDTA | 0.10 |
| Methylparaben | 0.15 |
| AJIDEW N-50 | 0.50 |
| Tapioca Fiber | 5.00 |
| Part B | |
| Sodium Laureth Sulfate | 30.00 |
| AMISOFT CT-12 | 10.00 |
| Cocamidopropyl Betaine | 5.00 |
| PEG-150 Distearate | 0.70 |
| Lauramide DEA | 2.00 |
| Part C | |
| Fragrance | 0.25 |
| KATHON CG II Biocide | 0.05 |
| Part D | |
| Sodium Chloride | 0.80 |

Procedure: Disperse polyquaternium-10 and tapioca fiber in deionized water. Heat to 70° C. Add remaining Part A ingredients and mix until uniform. Add Part B ingredients in order to the mixture. Mix at 70° C. until completely homogeneous and then cool to 40° C. Add Part C and mix well. Add Part D as needed to increase viscosity. Continue mixing and cooling to 35° C.

Example 8A

Example 8 is repeated with corn fiber in place of tapioca fiber.

Example 8B

Example 8 is repeated with rice fiber in place of tapioca fiber.

Example 8C

Example 8 is repeated with sago fiber in place of tapioca fiber.

Example 8D

Example 8 is repeated with pea fiber in place of tapioca fiber.

Example 8E

Example 8 is repeated with wheat fiber in place of tapioca fiber.

Example 8F

Example 8 is repeated with oat fiber in place of tapioca fiber.

Example 9

Tapioca Body Wash

TABLE 15

| Body Wash Formulation | |
|---|---|
| Ingredients Tradename/INCI name | Weight Percent |
| Water | 70.94 |
| STRUCTURE ® Plus polymer | 10.00 |
| Cocamidopropyl Betaine (30%) | 8.34 |
| Sodium $C_{14-16}$ Olefin Sulfonate (40%) | 14.47 |
| Disodium Laureth Sulfosuccinate (40%) | 5.25 |
| Tapioca Fiber | 10.00 |
| Glycerin | 1.00 |
| Citric Acid | Adjust to pH 6.0–6.5 |

Procedure: Disperse STRUCTURE® Plus polymer in water with mixing. Add remaining ingredients and mix until complete. Adjust pH with citric acid.

Example 9A

Example 9 is repeated with corn fiber in place of tapioca fiber.

Example 9B

Example 9 is repeated with rice fiber in place of tapioca fiber.

Example 9C

Example 9 is repeated with sago fiber in place of tapioca fiber.

Example 9D

Example 9 is repeated with pea fiber in place of tapioca fiber.

Example 9E

Example 9 is repeated with wheat fiber in place of tapioca fiber.

Example 9F

Example 9 is repeated with oat fiber in place of tapioca fiber.

Example 10

Tapioca Fiber Body Wash Shower Mousse

TABLE 16

| Body Wash Shower Mousse Formulation | |
|---|---|
| Ingredients Tradename/INCI Name | Weight Percent |
| STRUCTURE ® XL | 2.0 |
| Deionized water | 59.33 |
| Sodium Lauryl Sulfate (27.5%) | 21.42 |
| Tapioca Fiber | 4.00 |
| PLANATERIN 2000 (50%) | 4.00 |
| Propylene Glycol | 2.00 |
| Glycerine | 1.00 |
| UVINUL MS-40 | 0.05 |
| GERMABEN II | 0.20 |
| Isobutane | 6.00 |

Procedure: Slowly sift STRURCTURE® XL into water and mix until dispersed. Add all remaining ingredients (except isobutene), one at a time, mixing well after each addition. Mix entire batch until complete. Fill into cans and charge with isobutane propellant.

Example 10A

Example 10 is repeated with corn fiber in place of tapioca fiber.

Example 10B

Example 10 is repeated with rice fiber in place of tapioca fiber.

Example 10C

Example 10 is repeated with sago fiber in place of tapioca fiber.

Example 10D

Example 10 is repeated with pea fiber in place of tapioca fiber.

Example 10E

Example 10 is repeated with wheat fiber in place of tapioca fiber.

Example 10F

Example 10 is repeated with oat fiber in place of tapioca fiber.

Example 11

Tapioca Fiber Exfoliating Body Wash

TABLE 17

| Body Wash Formulation | |
|---|---|
| Ingredients Tradename/INCI Name | Weight Percent |
| Part A | |
| Distilled Water | 41.50 |
| Sodium Chloride | 0.50 |
| DISSOLVINE NA-2X | 0.20 |
| Tapioca Fiber | 7.00 |
| Part B | |
| STANDAPOL EA-2 | 24.00 |
| STANDAPOL A | 10.00 |
| MONATERIC CAB-LC | 2.00 |
| MONASIL PLN | 1.5 |
| Part C | |
| STRUCTURE ® Plus | 7.00 |
| Part D | |
| PROMIDIUM ® 2 | 2.00 |
| FLORABEADS Jojoba | 0.10 |
| Fragrance | 0.10 |

Procedure: Mix together Part A ingredients at room temperature until clear. Combine together the Part B ingredients and then add to Part A while stirring. Sift in Part C ingredient to the combined Part AB mixture with very slow mixing until clear. Premix Part D constituents and then add to Part ABC mixture with very slow mixing. Adjust pH to 6.0.

Example 11A

Example 11 is repeated with corn fiber in place of tapioca fiber.

Example 11B

Example 111 is repeated with rice fiber in place of tapioca fiber.

Example 11C

Example 11 is repeated with sago fiber in place of tapioca fiber.

Example 11D

Example 11 is repeated with pea fiber in place of tapioca fiber.

Example 11E

Example 11 is repeated with wheat fiber in place of tapioca fiber.

Example 11F

Example 11 is repeated with oat fiber in place of tapioca fiber.

Example 12

Tapioca Fiber in Make Up Remover

TABLE 18

| Make Up Remover Formulation | |
|---|---|
| Ingredients Tradename/INCI Name | Weight Percent |
| Part A | |
| Deionized Water | 83.75 |
| CARBOPOL 940 | 0.40 |
| Propylene Glycol | 3.00 |
| Part B | |
| ORMAGEL SH | 2.00 |
| CRODALAN AWS | 3.50 |
| Part C | |
| Deionized Water | 3.00 |
| TEA 99% | 0.60 |
| Part D | |
| Tapioca Fiber | 3.00 |

Procedure: premix Part A using high speed mixing and then heat to 75° C. Add Part B ingredients to Part A individually, mixing until homogeneous between each addition. Premix Part C and add to Part AB mixture with vigorous propeller mixing. Mix until smooth. Add Part D slowly to Parts ABC mixture with propeller mixing, allowing for uniform dispersion of fiber particles.

Example 12A

Example 12 is repeated with corn fiber in place of tapioca fiber.

Example 12B

Example 12 is repeated with rice fiber in place of tapioca fiber.

Example 12C

Example 12 is repeated with sago fiber in place of tapioca fiber.

Example 12D

Example 12 is repeated with pea fiber in place of tapioca fiber.

Example 12E

Example 12 is repeated with wheat fiber in place of tapioca fiber.

Example 12F

Example 12 is repeated with oat fiber in place of tapioca fiber.

Although the present invention has been described and illustrated in detail, it is to be understood that the same is by way of illustration and example only, and is not to be taken as a limitation. The spirit and scope of the present invention are to be limited only by the terms of any claims presented hereafter.

We claim:

1. A personal care composition comprising:
   a blend of starch and tapioca fiber, wherein tapioca fiber is present from about 2% to about 10%, said tapioca fiber comprising at least 10% by weight of a dietary fiber wherein said dietary fiber contains from about 33% to about 66% of insoluble fiber, wherein said starch is present from about 35% to about 70%; and
   a cosmetic ingredient;
   and wherein the personal care composition is a cleansing composition.

2. The cosmetic ingredient of claim 1 further comprising an aqueous solvent, non-aqueous solvent, pigment, surfactant, polymer, fragrance or combinations thereof.

3. The cleansing composition of claim 1 provides an increase in foaming and/or cleansing versus cleansing compositions without fiber.

4. The cleansing composition of claim 1 is selected from the group consisting of lotions, creams, mousse, body washes, bar soaps, and shampoos.

5. The cleansing composition of claim 1 wherein the personal care composition is an exfoliating cleansing composition.

6. The cleansing composition of claim 2 wherein the cosmetic ingredient is a polymer.

7. The cleansing composition of claim 6 wherein the polymer is a naturally derived polymer.

8. The cleansing composition of claim 2 wherein the cosmetic ingredient is a surfactant.

9. The cleansing Composition of claim 8 selected from the group consisting of a bar soap, bodywash and shampoo.

10. The cleansing composition of claim 9 a bar soap.

* * * * *

UNITED STATES PATENT AND TRADEMARK OFFICE
CERTIFICATE OF CORRECTION

| | |
|---|---|
| PATENT NO. | : 7,854,947 B2 |
| APPLICATION NO. | : 11/016031 |
| DATED | : December 21, 2010 |
| INVENTOR(S) | : Hongjie Cao, Gary T. Martino and Joanne Golas |

It is certified that error appears in the above-identified patent and that said Letters Patent is hereby corrected as shown below:

Col. 24, line 4,      delete "is" after claim 1

Col. 24, line 7,      delete "wherein the personal care composition" after claim 1

Signed and Sealed this
Tenth Day of May, 2011

David J. Kappos
*Director of the United States Patent and Trademark Office*

UNITED STATES PATENT AND TRADEMARK OFFICE
CERTIFICATE OF CORRECTION

PATENT NO. : 7,854,947 B2  
APPLICATION NO. : 11/016031  
DATED : December 21, 2010  
INVENTOR(S) : Cao et al.

Page 1 of 1

It is certified that error appears in the above-identified patent and that said Letters Patent is hereby corrected as shown below:

<u>Col. 24, line 16,</u>   change "Composition" to --composition--

<u>Col. 24, line 18,</u>   add "is" after claim 9

Signed and Sealed this
Thirty-first Day of May, 2011

David J. Kappos
*Director of the United States Patent and Trademark Office*